(12) United States Patent
Zimring

(10) Patent No.: US 10,830,777 B2
(45) Date of Patent: Nov. 10, 2020

(54) BIOCHEMICAL PREDICTORS OF RED BLOOD CELL QUALITY

(71) Applicant: Bloodworks, Seattle, WA (US)

(72) Inventor: James Charles Zimring, Seattle, WA (US)

(73) Assignee: Bloodworks, Seattle, WA (US)

( * ) Notice: Subject to any disclaimer, the term of this patent is extended or adjusted under 35 U.S.C. 154(b) by 292 days.

(21) Appl. No.: 15/760,780

(22) PCT Filed: Sep. 15, 2016

(86) PCT No.: PCT/US2016/051990
§ 371 (c)(1),
(2) Date: Mar. 16, 2018

(87) PCT Pub. No.: WO2017/048994
PCT Pub. Date: Mar. 23, 2017

(65) Prior Publication Data
US 2018/0252733 A1    Sep. 6, 2018

Related U.S. Application Data

(60) Provisional application No. 62/220,899, filed on Sep. 18, 2015.

(51) Int. Cl.
*A61K 35/18* (2015.01)
*G01N 33/80* (2006.01)
*G01N 33/49* (2006.01)
*G01N 33/50* (2006.01)

(52) U.S. Cl.
CPC ............ *G01N 33/80* (2013.01); *G01N 33/49* (2013.01); *G01N 33/50* (2013.01)

(58) Field of Classification Search
None
See application file for complete search history.

(56) References Cited

U.S. PATENT DOCUMENTS 9,903,876 B2 * 2/2018 Zimring ................ G01N 33/53
2013/0130298 A1 5/2013 Tarasev et al.
2014/0178904 A1 6/2014 Zimring

FOREIGN PATENT DOCUMENTS

WO    WO 2016/023042 A1    2/2016

OTHER PUBLICATIONS

PCT International Search Report and Written Opinion, International Application No. PCT/US2016/051990, dated Dec. 2, 2016, 17 pp.

Dern and Wiorkowski, "Studies on the preservation of human blood. IV. The hereditary component of pre- and poststorage erythrocyte adenosine triphosphate levels," J. Lab. Clin. Med., vol. 73, No. 6, 1969, pp. 1019-1029.

Dern, et al., "Studies on the preservation of human blood. I. Variability in erythrocyte storage characteristics among healthy donors," J. Lab. Clin. Med., vol. 67, No. 6, 1966, pp. 955-965.

Dumont and AuBuchon, "Evaluation of proposed FDA criteria for the evaluation of radiolabeled red cell recovery trials," Transfusions, vol. 48, No. 6, 2008, pp. 1053-1060.

Office Action dated Feb. 15, 2019 for European Application No. 13832087.4, 3 pages.

Fergusson, et al., "Effect of fresh red blood cell transfusions on clinical outcomes in premature, very low-birth-weight infants: the ARIPI randomized trial," JAMA, vol. 308, No. 14, 2012, pp. 1443-1451.

Gilson, et al., "A novel mouse model of red blood cell storage and posttransfusion in vivo survival," Transfusion, vol. 49, No. 8, 2009, pp. 1546-1553.

Hess, "Red cell changes during storage," Transfus. Apher. Sci., vol. 43, No. 1, 2010, pp. 51-59.

Hess, "Red cell storage," J. Proteomics, vol. 73, No. 3, 2010, pp. 368-373.

Hess, "Scientific problems in the regulation of red blood cell products," Transfusion, vol. 52, No. 8, 2012, pp. 1827-1835.

Hod and Spitalnik, "Harmful effects of transfusion of older stored red blood cells: iron and inflammation," Transfusion, vol. 51, No. 4, 2011, pp. 881-885.

Hod and Spitalnik, "Stored red blood cell transfusions: Iron, inflammation, immunity, and infection," Transfus. Clin. Biol., vol. 19, No. 3, 2012, pp. 84-89.

Hod, et al., "Transfusion of human volunteers with older, stored red blood cells produces extravascular hemolysis and circulating non-transferrin-bound iron," Blood, vol. 118, No. 25, 2011, pp. 6675-6682.

Hod, et al., "Transfusion of red blood cells after prolonged storage produces harmful effects that are mediated by iron and inflammation," Blood, vol. 115, No. 21, 2010, pp. 4284-4292.

Kor, et al., "Red blood cell storage lesion," Bosn. J. Basic Med. Sci., vol. 9, Suppl 1, 2009, pp. 21-27.

Lacroix, et al., "The Age of Blood Evaluation (ABLE) randomized controlled trial: study design," Transfus. Med. Rev., vol. 25, No. 3, 2011, pp. 197-205.

Reid, et al., "The viability of autologous human red cells stored in additive solution 5 and exposed to 25 degrees C for 24 hours," Transfusion, vol. 39, No. 9, 1999, pp. 991-997.

(Continued)

*Primary Examiner* — Gary Counts
(74) *Attorney, Agent, or Firm* — Lee & Hayes PC; C. Rachal Winger; Thu Nguyen

(57) ABSTRACT

Compositions and methods for determining post-transfusion survival or toxicity of red blood cells and the suitability of red blood cell units for transfusion by measuring the levels of one or more compounds in a red blood cell sample are provided.

8 Claims, No Drawings

(56) References Cited

OTHER PUBLICATIONS

Silliman, "Lipids: free fatty acids, eicosanoids, and lysophospholipids and the pro-inflammatory effects of transfusion," ASH Meeting, Scientific Program, 2012, SCI-48.
Silliman, et al., "Identification of lipids that accumulate during the routine storage of prestorage leukoreduced red blood cells and cause acute lung injury," Transfusion, vol. 51, 2011, pp. 2549-2554.
Steiner, et al., "Addressing the question of the effect of RBC storage on clinical outcomes: the Red Cell Storage Duration Study (RECESS) (Section 7)," Transfus. Apher. Sci., vol. 43, No. 1, 2010, pp. 107-116.
Tissot, et al., "Analysis and clinical relevance of microparticles from red blood cells," Curr. Opin. Hematol., vol. 17, No. 6, 2010, pp. 571-577.
Van de Watering, "Red cell storage and prognosis," Vox Sang., vol. 100, No. 1, 2011, pp. 36-45.
Van de Watering, et al., "Pitfalls in the current published observational literature on the effects of red blood cell storage," Transfusion, vol. 51, No. 8, 2011, pp. 1847-1854.
Zimring, et al., "Strain-specific red blood cell storage, metabolism, and eicosanoid generation in a mouse model," Transfusion, vol. 54, No. 1, 2014, pp. 137-148.

\* cited by examiner

BIOCHEMICAL PREDICTORS OF RED BLOOD CELL QUALITY

FIELD

The disclosed subject matter relates to compositions and methods for determining post-transfusion survival and toxicity of red blood cell (RBC) units by measuring the levels of one or more compounds in a RBC sample.

BACKGROUND

In excess of 15,000,000 units of RBCs are transfused in the USA each year into an excess of 5,000,000 patients (approximately 1 out of every 65 Americans). Currently, there are only 3 quality control measures utilized prior to release of a unit of RBCs: 1) testing negative for the screened pathogens, 2) compatibility with the patient regarding recipient antibodies to donor antigens, and 3) storage history of 4° C. FDA guidelines for RBC storage require that stored RBCs (up to 42 days) have less than 1% homolysis and have 75% 24 hour post-transfusion survival, on average for a given storage system. However, it has been appreciated for over forty years that there is tremendous variability in how individual units of RBCs store from different human donors[1,2]. Even for current blood storage solutions, 24 hour post-transfusion recoveries range from 35% to 100%[2] It has been further observed that RBC storage is reproducible from donation to donation for a given donor[3,4], suggesting a potential genetic component[1,5].

SUMMARY

Described herein are compositions and methods for determining post-transfusion survival and toxicity of a RBC unit by measuring the levels of one or more markers in a RBC sample.

In a first aspect, disclosed herein is a method of determining post-transfusion survival of red blood cells (RBC) prior to transfusion, the method including the steps of: a) measuring the levels of one or more markers in a RBC sample selected from the group consisting of the compounds shown in Table 1, and the reticulocyte count of a blood donor at the time of donation, b) comparing the level of the one or more markers in the RBC sample with the level of the one or more markers present in a control sample, wherein a higher or lower level of the one or more markers in the RBC sample is indicative of a lower RBC storage quality.

In a second aspect, disclosed herein is a method of determining the suitability of a red blood cell (RBC) unit for transfusion, the method including the steps of: a) measuring the levels of one or more markers in a RBC sample selected from the group consisting of the compounds shown in Table 1, and the reticulocyte count of a blood donor at the time of donation; b) comparing the level of the one or more markers in the RBC sample with the level of the one or more markers present in a control sample, wherein a higher or lower level of the one or more markers in the RBC sample is indicative of a lower suitability for transfusion.

In various embodiments of the first and second aspects, the measurement is performed at the time of collection of the RBC sample.

In various embodiments of the first and second aspects, the measurement is performed during the time of storage of the RBC sample.

In various embodiments of the first and second aspects, the measurement is performed by mass spectrometry. In various embodiments, the mass spectrometry is gas-chromatography/mass spectrometry (GC/MS) or liquid chromatography-tandem mass spectrometry (LC/MS/MS).

In various embodiments of the first and second aspects, the measurement is performed by enzymatic assay.

In various embodiments of the first and second aspects, the measurement is performed by ELISA.

In various embodiments of the first and second aspects, the level of the one or more marker is 2-200 fold higher than in the control sample.

In a third aspect, disclosed herein is method for determining RBC storage quality, the method including the steps of: obtaining a dataset associated with a sample of stored blood, wherein the dataset includes at least one marker, selected from the group consisting of the compounds shown in Table 1, and the reticulocyte count of a blood donor at the time of donation; analyzing the dataset to determine data for the at least one marker, wherein the data is positively correlated or negatively correlated with RBC storage quality of the sample of stored blood.

In a fourth aspect, disclosed herein is method for determining RBC storage quality, the method including the steps of: obtaining a sample of stored blood, wherein the sample includes at least one marker, selected from the group consisting of the compounds shown in Table 1, and the reticulocyte count of a blood donor at the time of donation, and the reticulocyte count of a blood donor at the time of donation; contacting the sample with a reagent; generating a complex between the reagent and the at least one marker; detecting the complex to obtain a dataset associated with the sample, wherein the dataset includes expression or activity level data for the at least one marker; and analyzing the expression or activity level data for the at least one marker, wherein the expression or activity level of the at least one marker is positively correlated or negatively correlated with RBC storage quality.

In a fifth aspect, disclosed herein is computer-implemented method for determining RBC storage quality, the method including the steps of: storing, in a storage memory, a dataset associated with a stored blood sample, wherein the dataset includes data for at least one marker, selected from the group consisting of the compounds shown in Table 1, and the reticulocyte count of a blood donor at the time of donation, and the reticulocyte count of a blood donor at the time of donation; and analyzing, by a computer processor, the dataset to determine the expression or activity levels of the at least one marker, wherein the expression or activity levels are positively correlated or negatively correlated with RBC storage quality.

In a sixth aspect, disclosed herein is system for determining RBC storage quality, the system including: a storage memory for storing a dataset associated with a stored blood sample, wherein the dataset includes data for at least one marker, wherein the dataset includes data for at least one marker, selected from the group consisting of the compounds shown in Table 1, and the reticulocyte count of a blood donor at the time of donation, and the reticulocyte count of a blood donor at the time of donation; and a processor communicatively coupled to the storage memory for analyzing the dataset to determine the activity or expression levels of the at least one marker, wherein the activity or expression levels are positively correlated or negatively correlated with RBC storage quality.

In a seventh aspect, disclosed herein is computer-readable storage medium storing computer-executable program code, the program code including: program code for storing a dataset associated with a stored blood sample, wherein the dataset includes data for at least one marker, wherein the dataset includes data for at least one marker, selected from the group consisting of the compounds shown in Table 1, and the reticulocyte count of a blood donor at the time of donation, and the reticulocyte count of a blood donor at the time of donation; and program code for analyzing the dataset to determine the activity or expression levels of the at least one marker, wherein the activity or expression levels of the markers are positively correlated or negatively correlated with RBC storage quality.

In an eighth aspect, disclosed herein is method for predicting a negative transfusion outcome, the method including the steps of: obtaining a dataset associated with a sample of stored blood, wherein the dataset includes at least one marker, wherein the dataset includes data for at least one marker, selected from the group consisting of the compounds shown in Table 1, and the reticulocyte count of a blood donor at the time of donation, and the reticulocyte count of a blood donor at the time of donation; analyzing the dataset to determine data for the at least one marker, wherein the data is positively correlated or negatively correlated with a negative transfusion outcome if the blood sample is transfused into a patient.

In a ninth aspect, disclosed herein is method for predicting a negative transfusion outcome, the method including the steps of: obtaining a sample of stored blood, wherein the sample includes at least one marker, wherein the dataset includes data for at least one marker, selected from the group consisting of the compounds shown in Table 1, and the reticulocyte count of a blood donor at the time of donation, and the reticulocyte count of a blood donor at the time of donation; contacting the sample with a reagent; generating a complex between the reagent and the at least one marker; detecting the complex to obtain a dataset associated with the sample, wherein the dataset includes expression or activity level data for the at least one marker; and analyzing the expression or activity level data for the markers, wherein the expression or activity level of the at least one marker is positively correlated or negatively correlated with a negative transfusion outcome if the blood sample is transfused into a patient.

In a tenth aspect, disclosed herein is computer-implemented method for predicting a negative transfusion outcome, the method including the steps of storing, in a storage memory, a dataset associated with a stored blood sample, wherein the dataset includes data for at least one marker wherein the dataset includes data for at least one marker, selected from the group consisting of the compounds shown in Table 1, and the reticulocyte count of a blood donor at the time of donation, and the reticulocyte count of a blood donor at the time of donation; and analyzing, by a computer processor, the dataset to determine the expression or activity levels of the at least one marker, wherein the expression or activity levels are positively correlated or negatively correlated with a negative transfusion outcome if the blood sample is transfused into a patient.

In an eleventh aspect, disclosed herein is system for predicting a negative transfusion outcome, the system including: a storage memory for storing a dataset associated with a stored blood sample, wherein the dataset includes data for at least one marker, wherein the dataset includes data for at least one marker, selected from the group consisting of the compounds shown in Table 1, and the reticulocyte count of a blood donor at the time of donation, and the reticulocyte count of a blood donor at the time of donation; and a processor communicatively coupled to the storage memory for analyzing the dataset to determine the activity or expression levels of the at least one marker, wherein the activity or expression levels are positively correlated or negatively correlated with a negative transfusion outcome if the blood sample is transfused into a patient.

In a twelfth aspect, disclosed herein is computer-readable storage medium storing computer-executable program code, the program code including: program code for storing a dataset associated with a stored blood sample, wherein the dataset includes data for at least one marker, selected from the group consisting of the compounds shown in Table 1, and the reticulocyte count of a blood donor at the time of donation, and the reticulocyte count of a blood donor at the time of donation; and program code for analyzing the dataset to determine the activity or expression levels of the at least one marker, wherein the activity or expression levels of the markers are positively correlated or negatively correlated with a negative transfusion outcome if the blood sample is transfused into a patient.

In various embodiments of the above aspects, the dataset is obtained at the time of collection of the RBC sample.

In various embodiments of the above aspects, the dataset is obtained during the time of storage of the RBC sample.

In various embodiments of the above aspects, the dataset is obtained by mass spectrometry.

In various embodiments of the above aspects, the mass spectrometry is gas-chromatography/mass spectrometry (GC/MS) or liquid chromatography-tandem mass spectrometry (LC/MS/MS).

In various embodiments of the above aspects, the dataset is obtained by enzymatic assay.

In various embodiments of the above aspects, the dataset is obtained by ELISA.

In a thirteenth aspect, disclosed herein is a method for determining post-transfusion survival of red blood cells (RBC) prior to transfusion including: a) generating data on the level of one or more markers in a RBC sample selected from the group consisting of the compounds shown in Table 1, and the reticulocyte count of a blood donor at the time of donation, and the reticulocyte count of a blood donor at the time of donation; b) generating a score by mathematically combining the data in (a), wherein the score is indicative of post-transfusion survival of red blood cells (RBC) in the sample.

In some embodiments of this aspect, the score is used to determine whether the RBC sample will be administered to the subject. In some embodiments, the score is generated by a computer processor.

In various embodiments of the above aspects, the method further includes the step of administering or not administering the RBC sample that has been tested.

In a fourteenth aspect, disclosed herein is a kit for use in predicting a negative transfusion outcome or red blood cell (RBC) storage quality, the kit including: a set of reagents including a plurality of reagents for determining from a stored blood sample data for at least one marker, selected from the group consisting of the compounds shown in Table 1, and the reticulocyte count of a blood donor at the time of donation, and the reticulocyte count of a blood donor at the time of donation; and instructions for using the plurality of reagents to determine data from the stored blood sample.

DETAILED DESCRIPTION

The presently disclosed subject matter generally relates to compositions and methods for determining post-transfusion survival and toxicity of RBCs by measuring the levels of one or more compounds in a RBC sample.

Before the presently disclosed subject matter is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the presently disclosed subject matter will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the presently disclosed subject matter, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the presently disclosed subject matter is not entitled to antedate such publication by virtue of prior invention. Further, the dates of publication provided can be different from the actual publication dates which can need to be independently confirmed.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the presently disclosed subject matter. Any recited method can be carried out in the order of events recited or in any other order which is logically possible.

The subject matter described in this disclosure represents a method for assessing an RBC unit (prior to transfusion) allowing the prediction of both its post-transfusion RBC survival and also the generation of toxic byproducts, including bioactive lipids.

Red blood cell (RBC) transfusion is a life-saving therapy, and refrigerated storage is crucial for maintaining an adequate supply of donor units. However, recent studies have focused on potential adverse clinical sequelae resulting from transfusing humans with RBC units stored for longer periods of time. Indeed, multiple observational studies in human patients provide data demonstrating inferior clinical outcomes when older, stored RBC units are transfused[10]. Nonetheless, this issue remains controversial because other, similarly designed human studies, show no difference in clinical outcome when comparing patients receiving transfusions of older or fresher RBC units[10,11]. To begin to address this controversy, several prospective human trials are currently ongoing, and one was recently completed[12-14]. However, it is not controversial that stored RBCs accumulate multiple factors that may be toxic when infused (e.g. microparticles, free iron, free hemoglobin, prostaglandins, and leukotrienes)[15-23].

One complication in studying RBC transfusion is that there is considerable donor-to-donor variation in the effect of refrigerated storage on RBC function and quality. In addition, there is a general absence of robust analytic tests that consistently and accurately predict the quality of a given RBC unit prior to transfusion[24]. Due to the genetic and environmental complexity of outbred human donor populations, and the difficulty in limiting the number of independent variables in studying human RBC transfusion, we developed a robust animal model to begin to address these issues[25]. Using inbred mouse strains in defined environmental and dietary settings limits the experimental variability of the system, and allows for deliberate manipulation of independent variables. This was combined with metabolomic methods to determine whether variations in the levels, and/or changes in concentrations, of small molecules in vitro correlated with post-transfusion RBC recovery in vivo. In particular, we can evaluate whether: 1) genetic background correlated with donor RBC storage quality, 2) metabolomic differences correlated with donor RBC storage quality, and 3) accumulation of potentially toxic molecules correlated with genetic background and/or donor RBC storage quality.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the presently disclosed subject matter, the preferred materials and methods are described herein.

As used herein, "RBC storage quality" is defined as the extent of post-transfusion recovery of the stored RBCs, higher recovery is defined as higher quality. Examples of post-transfusion recovery include greater than zero and almost 100% recovery, i.e., recovery of 10%, 20%, 30%, 40%, 50%, 60%, 70%, 80%, 90%, 100%, and all percentages in between. In one embodiment, an acceptable RBC storage quality is an average of 75% post-transfusion recovery at 24 hours, as under FDA guidelines. A RBC sample determined to have lower RBC storage quality will generally be excluded from being used in a transfusion.

As used herein, "toxicity" of a RBC unit is defined as any adverse reaction associated with transfusion of a RBC unit, including, but not limited to, hemolytic transfusion reactions, exposure to free hemoglobin, iron overload, induction of recipient cytokines, introduction of procoagulant activity, and inhibition of recipient vascular relaxation, among others.

As used herein, a RBC unit is less suitable for transfusion if it has lower RBC quality (i.e., post-transfusion survival) or elevated toxicity as compared to other RBC units, e.g., as compared to a control. A RBC sample determined to be less suitable for transfusion as determined herein will generally excluded from being used in a transfusion.

An "analyte" or "target" refers to a compound to be detected. Such compounds can include small molecules, peptides, proteins, nucleic acids, as well as other chemical entities. In the context of the presently disclosed subject matter, an analyte or target will generally correspond to the biochemical compounds disclosed herein, or a reaction product thereof.

The term "biomarker" refers to a molecule (typically small molecule, protein, nucleic acid, carbohydrate, or lipid) that is expressed and/or released from a cell, which is useful for identification or prediction. Such biomarkers are molecules that can be differentially expressed, e.g., overexpressed or underexpressed, or differentially released in response to varying conditions (e.g., storage). In the context of the presently disclosed subject matter, this frequently refers to the biochemical compounds disclosed herein, which are elevated or decreased in stored versus non-stored RBCs, for instance, 1-fold, 2-fold, 3-fold, 4-fold, 5-fold or more in stored RBCs versus non-stored RBCs.

A "sample" refers to any source which is suspected of containing an analyte or target molecule. Examples of samples which may be tested using the presently disclosed subject matter include, but are not limited to, blood, serum, plasma, urine, saliva, cerebrospinal fluid, lymph fluids, tissue and tissue and cell extracts, cell culture supernatants, among others. A sample can be suspended or dissolved in liquid materials such as buffers, extractants, solvents, and the like. In the context of the present application, a sample is generally a stored RBC sample of varying length of storage.

"Antibody" refers to any immunoglobulin or intact molecule as well as to fragments thereof that bind to a specific epitope that may be used in the practice of the presently disclosed subject matter. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term and may be used in the practice of the disclosed subject matter, including IgA, IgD, IgE, IgG, and IgM.

An "antibody fragment" refers specifically to an incomplete or isolated portion of the full sequence of the antibody which retains the antigen binding function of the parent antibody and may also be used in the presently disclosed subject matter. Examples of antibody fragments include Fab, Fab', F(ab')2, and Fv fragments; diabodies; linear antibodies; single-chain antibody molecules; and multispecific antibodies formed from antibody fragments.

An intact "antibody" for use in the disclosed subject matter includes at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus films in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a $F(ab')_2$ fragment, a bivalent fragment including two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

"Single chain antibodies" or "single chain Fv (scFv)" may also be used in the presently disclosed subject matter. This term refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments can be prepared by recombinant techniques or enzymatic or chemical cleavage of intact antibodies.

A "monoclonal antibody" may be used in the presently disclosed subject matter. Monoclonal antibodies are a preparation of antibody molecules of single molecular composition. A monoclonal antibody composition displays a single binding specificity and affinity for a particular epitope.

In one embodiment, the antibody or fragment is conjugated to an "effector" moiety. The effector moiety can be any number of molecules, including labeling moieties such as radioactive labels or fluorescent labels.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

Samples of RBCs stored for various amounts of time are compared to "control" samples which can be freshly drawn RBCs or RBCs which have been minimally stored. Control samples are assigned a relative analyte amount or activity to which sample values are compared. Relevant levels of analyte elevation occur when the sample amount or activity value relative to the control is 110%, more preferably 150%, more preferably 200-500% (i.e., two to five fold higher relative to the control), more preferably 1000-3000% higher.

Assays for many of the biochemical compounds disclosed herein are known or commercially available.

For example, antibody reagents can be used in assays to detect the levels of analytes in RBC samples using any of a number of immunoassays known to those skilled in the art.

According to some embodiments, the disclosure includes methods for determining the suitability of a stored blood sample including red blood cells (RBCs) for use in a blood transfusion. Such a method can include measuring a level of one or more markers in the stored blood sample and/or comparing the level of the one or more markers in the stored blood sample with a level of the one or more markers present in a control blood sample determined to be suitable for use in a blood transfusion. Such a method can also include measuring a level of two or more markers in the stored blood sample and/or comparing the level of the two or more markers in the stored blood sample with a level of the two or more markers present in a control blood sample determined to be suitable for use in a blood transfusion. The subject methods can also include generating an integrated sample score from the level of the two or more markers in the stored blood sample and/or control sample by, for example, adding the respective levels for a sample, and comparing the score of each to determine a higher or lower RBC storage quality. In some versions a higher integrated sample score indicates a higher level of the two or more markers in the stored blood sample, such as the markers set forth in Table 1, compared to the control blood sample. In some versions a lower integrated sample score indicates a lower level of the two or more markers in the stored blood sample, such as the markers set forth in Table 1, compared to the control blood sample.

The methods also can include determining a higher level of the one or more, e.g., two or more, markers in the stored blood sample, such as the markers set forth in Table 1, compared to the control blood sample that indicates a lower RBC storage quality of the RBCs of the stored blood sample as compared to RBCs of the control blood sample and thereby predicting a lower post-transfusion survival of the of the RBCs of the stored blood sample than RBCs of the control blood sample, and/or determining an absence of a higher level, e.g., an equal and/or lower level, of the one or more markers in the stored blood sample compared to the control blood sample, which is indicative of a higher RBC storage quality. The methods also can include excluding the stored blood sample from use in the blood transfusion when a lower RBC storage quality of the RBCs of the stored blood sample is indicated as compared to the RBCs of the control blood sample, and/or using the stored blood sample in the blood transfusion when an absence of a higher level of the one or more markers in the stored blood sample compared to the control blood sample and/or a higher RBC storage quality is determined.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); immunohistochemical (IHC) assays; capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997). Liposome immunoassays, such as flow-injection liposome immunoassays and liposome immunosensors, are also suitable for use in the presently disclosed subject matter. See, e.g., Rongen et al., J. Immunol. Methods, 204:105-133 (1997). In addition, nephelometry assays, in which the formation of protein/antibody complexes results in increased light scatter that is converted to a peak rate signal as a function of the marker concentration, are suitable for use in the methods of the presently disclosed subject matter. Nephelometry assays are commercially available from Beckman Coulter (Brea, Calif.; Kit #449430) and can be performed using a Behring Nephelometer Analyzer (Fink et al., J. Clin. Chem. Clin. Biochem., 27:261-276 (1989)).

Specific immunological binding of the antibody to proteins can be detected directly or indirectly. Direct labels include fluorescent or luminescent tags, metals, dyes, radionuclides, and the like, attached to the antibody. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the presently disclosed subject matter can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

In some embodiments, the measurement of the markers of the presently disclosed subject matter is performed using various mass spectrometry methods. As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces," U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21; 1164-67.

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

In some embodiments, the presently disclosed subject matter is practiced using computer implementation. In one embodiment, a computer includes at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The following examples of specific aspects for carrying out the presently disclosed subject matter are offered for illustrative purposes only, and are not intended to limit the scope of the presently disclosed subject matter in any way.

Utility

Despite extensive study, there is no measurable entity known to predict how an RBC unit will do when transfused. For this reason, currently, there are no quality control measures (or unit release criteria) regarding quality of RBC units. This is a medical problem since RBCs that survive poorly post-transfusion result in a less efficacious product from the standpoint of RBC replacement. Thus the lack of reliable biochemical markers is an impediment to patient care and identification of such markers would have high clinical utility.

A related and highly relevant issue is the potential untoward effects of storing RBCs, which leads to the build-up of toxic products in the RBC units, and may result in potential morbidity and/or mortality as a direct toxicological insult in the recipient. In particular, it has been well described that bioactive lipids are generated over the storage of both human RBCs and also in rodent models of RBC storage[6,7]. Such lipids, including eicosanoids and lysophospholipids, can induce inflammation which may contribute to a number of sequelae, including (but not limited to) initiation and/or exacerbation of transfusion related acute lung injury.

There are currently no existing techniques to predict post-transfusion survival of RBC units or toxicity of said units. Thus, the present disclosure satisfies these and other needs. Disclosed herein is a method for assessing a RBC unit (prior to transfusion) allowing the prediction of its post-transfusion survival and toxicity. Specifically, biochemical compounds that predict if RBCs will survive well post-transfusion or will be toxic are presented herein.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Materials and Methods

Mice: The following strains of mice were purchased from Jackson Labs (Bar Harbor, Me.): KK/HIJ Jax #002106, LG/J Jax #000675, AKR/J Jax #000648, FVB/NJ Jax #001800, C3H/HeJ Jax #000659, DBA/2J Jax #000671, NOD/ShiLtJ Jax #001976, 129X1/SvJ Jax #000691, 129S1/SvImJ Jax #002448, A/J Jax #000646, BTBR/T+ tf/J Jax #002282, Balb/cByJ Jax #001026, C57B1/6J Jax #000664). All were female and used for blood donation at 12-15 weeks of age UbiC-GFP male mice (Jackson stock #004353), which are on a C57/BL/6 background, were bred to FVB/NJ females (Jackson #001800) in the Bloodworks NW Research Institute (BWNWRI) Vivarium and offspring were used as RBC recipients at 24-28 weeks of age. HOD mice, used as a tracer population for transfused RBCs, were likewise bred in the BWNWRI Vivarium. The HOD mouse was first described on an FVB background, but has now been backcrossed onto C57BL6J for greater than 20 generations. All mice were maintained on standard rodent chow and water in a temperature- and light-controlled environment. All experiments were performed according to approved Institutional Animal Care and Use Committee (IACUC) procedures.

Collection and Storage of Blood: For each experimental rendition, RBCs (600 µl) were collected via cardiac puncture from one individual donor mouse from each strain into 84 µl CPDA-1 (12.3%) in a sterile 1.7 ml snapcap microcentrifuge tube. Hematocrits were adjusted to approximately 75% and samples were stored for seven days at 4° C. After storage, 50 µl stored RBCs were resuspended in 510 µl PBS and 5 µl of HOD packed RBCs were added to the suspension (in order to provide an internal control). The mixture of RBCs was then directly transfused into FVB/NJ×UbiC-GFP recipients by intravenous tail vein injection so that one recipient received a transfusion from one individual donor. The remaining sample of stored RBCs were snap frozen in liquid nitrogen for future metabolomics analysis. (Fresh renditions followed the same protocol but were transfused and snap frozen on the day of collection.) Ratios of donor blood to HOD tracer RBCs was enumerated, both at baseline in the cells to be transfused (pre-transfusion mixture) and also in peripheral blood acquired from recipients 24 hours after transfusion (post-transfusion samples collected into ACD). Pre-transfusion and post-transfusion RBCs were washed 3× with PBS, and stained for 30 mins with 0.5 µg anti-Fy3 (clone MIMA29) in 50 µl PBS. Stained cells were then washed 3× with PBS and incubated with 0.2 µg APC Goat-anti-mouse Igs (BD Cat. 550826) in 50 µl PBS for 30 mins, which stains RBCS bound with MIMA-29 and thus labels HOD tracer RBCs. Cells were then washed 3 times, re-suspended in PBS, and analyzed by flow cytometry (500 HOD+ events were counted for each sample). This approach utilizes MIMA29 to stain HOD tracer RBCs with a color that is different than the GFP RBCs, which fluoresce spontaneously. Final RBC survival was calculated by the formula: (GFP RBC/HOD RBC of post-transfusion sample)/(GFP/HOD pre-transfusion sample).

For a given experiment, all transfusions were performed with the same RBC preparation and after either seven days storage or on the same day (within a span of 1.5 hours). Three renditions were completed for both fresh and stored samples.

Example 2

Assessment of Post-Transfusion RBC Recovery and Endogenous RBC Lifespan

We have previously described the development of RBC storage models in mice[8]. Moreover, we have described that like human donor variability, RBCs from genetically distinct strains of mice have very different storage characteristics[9]. In particular, we have reported that RBCs from C57BL/6 mice store well, whereas RBCs from FVB mice store very poorly by comparison[9]. This extends both to RBC post-transfusion survival and also to the generation of lysolipids, and eicosanoids (e.g. prostaglandins and leukotrienes) that are known to affect inflammation, coagulation, vascular biology and immunity. To generate a genetically divergent population, we crossed B6×FVB mice to obtain F1 mice that are also genetically identical, as for each numbered chromosome, one comes from B6 and the other from FVB parents. F1 mice were then interbred to generate an F2 population that had a random segregation of chromosomes, including additional genetic diversity due to crossing over events. Methods were developed to allow RBC storage from single donor mice, and 154 F2 animals were tested. Stored RBCs were assayed for spontaneous hemolysis and also transfused into recipient mice to calculate 24 hour post-transfusion recoveries. Prior to transfusion, a sample of each donor's RBCs were subjected to LC-MS/MS to generate an untargeted metabolomics profile.

For all RBC storage experiments, donor mouse RBCs were stored at 4° C. for 7 days; this time frame was previously identified, using C57/BL6J mouse donor RBCs, as appropriately approximating the refrigerated shelf life identified by the Food and Drug Administration for human RBCs; that is, on average, 75% of donor mouse RBCS were still circulating 24 hr post-transfusion at the Day 7 "outdate." Therefore, at Day 7 of storage, 100 µl of stored, donor, packed RBCs (i.e. one mouse "unit") were transfused into H2-$K^b$ GFP+ recipient mice. At 10 min, 30 min, 1 hr, 4 hr, and 24 hr post-transfusion, peripheral blood was obtained from recipients, and transfused RBC's were enumerated by flow cytometry by gating on GFP-negative RBC events.

Peripheral blood obtained from non-transfused mice was used to enumerate the low number of events in the GFP-negative gate, which were then subtracted from the analysis of transfused RBCs.

For determination of endogenous RBC lifespan, mice received 3 daily injections of NHS-biotin i.p. (Pierce, Thermo Scientific) until ~100% of circulating RBCs were reactive with avidin-allophycocyanin, as assessed by flow cytometry. Peripheral RBCs were then obtained weekly and stained with avidin-allophycocyanin, followed by enumeration of positive and negative RBCs by flow cytometry. These data were then plotted to determine RBC lifespan.

Mass Spectrometry Analysis of RBC Samples

Donor RBC samples, freshly obtained and at various times after refrigerated storage, were rapidly frozen using dry ice/ethanol and stored at 80° C. The supernatant was not stored separately nor were the RBCs washed and stored separately; thus, the results obtained evaluated the metabolites in the entire "unit." Samples were shipped on dry ice to Metabolon Inc., where they were split into equal parts for analysis by gas-chromatography/mass spectrometry (GC/MS) and liquid chromatography-tandem mass spectrometry (LC/MS/MS). The LC/MS/MS platform was based on a Waters ACQUITY UPLC and a Thermo-Finnigan LTQ mass spectrometer, which consisted of an electrospray ionization (ESI) source and linear ion-trap (LIT) mass analyzer. The sample extract was split into two aliquots, dried, and then reconstituted in acidic or basic LC-compatible solvents, each of which contained 11 or more injection standards at fixed concentrations. One aliquot was analyzed using acidic positive-ion optimized conditions and the other using basic negative-ion optimized conditions in two independent injections using separate dedicated columns. Extracts reconstituted in acidic conditions were gradient eluted using water and methanol, both containing 0.1% Formic acid, whereas the basic extracts, which also used water/methanol, contained 6.5 mM Ammonium Bicarbonate. The MS analysis alternated between MS and data-dependent $MS^2$ scans using dynamic exclusion. The samples destined for GC/MS analysis were re-dried under vacuum desiccation for a minimum of 24 hr prior to being derivatized under dried nitrogen using bistrimethyl-silyl-triflouroacetamide. The GC column was 5% phenyl and the temperature ramp was from 40° to 300° C. in a 16 minute period. Samples were analyzed on a Thermo-Finnigan Trace DSQ fast-scanning single-quadrupole mass spectrometer using electron impact ionization. Compounds were identified by comparison to library entries of purified standards or recurrent unknown entities. Identification of known chemical entities was based on comparison to metabolomic library entries of purified standards. As of the time of analysis, more than 1000 commercially-available purified standard compounds had been acquired and registered into LIMS for distribution to both the LC and GC platforms for determination of their analytical characteristics. The combination of chromatographic properties and mass spectra gave an indication of a match to the specific compound or an isobaric entity.

The peak areas for each identified biochemical entity were log transformed, scaled to the median value for each compound observed in the experiment, and normalized to Bradford protein content; results below the limit of detection were imputed with the minimum observed value for the compound. A Two-Way ANOVA with Contrasts was used to determine the significance of variable main effects (e.g. Condition or Time/Day) and their interaction, and to identify biochemical entities that differed significantly between experimental groups ($p \leq 0.05$). An estimate of the false discovery rate (q-value) is calculated to take into account the multiple comparisons that normally occur in metabolomic-based studies.

RBCs from F2 mice had a near Gaussian distribution of 24-hr recoveries and homolysis, LC-MS/MS quantified 554 analytes in each stored RBC sample. Metabolomics analysis revealed that the analytes with the strongest correlation to post-transfusion survival of RBCs were a wide variety of compounds. Table 1 shows the compounds that had the strongest correlations (both positive and negative) with RBC post-transfusion survival. Correlations represent r values as calculated by the Pearson method. Absolute values of correlation are utilized to generate a rank order of correlation; some compounds correlate positively, while others are negative correlations.

More specifically, in this study, metabolites were chosen based upon the following criteria (correlation greater than 0.5 or less than −0.5, p value <0.05, q value <0.01). Using these criteria, 14 metabolites had a positive correlation with RBC storage, all with p values <0.0005 and q values <0.003 (See Table 1).

24 metabolites had a negative correlation that fit the above criteria.

Example 3

Application of the Above Markers as a Diagnostic Test of RBC Units

The above markers of RBC unit quality may be applied to evaluation of RBC units in several different ways. First, a sample of an RBC unit can be subjected to mass spectrometry and the profile of the above markers can be generated (all from a single sample). This profile would then be used to predict the post-transfusion survival of the RBC unit. Such information would allow several distinct medical advantages, for example:
1) Direction of better units of RBCs to patients whose disease status makes chronic transfusion load dangerous (e.g. iron overload).
2) identifying units that had increased accumulation of toxic lipids that may lead to untoward effects such as TRALI, and avoiding their transfusion into vulnerable patient populations.
3) Management of the blood supply such that storage time (outdate) for individual units could be tailored to the biology of the unit. The metric for a viable unit would no longer be its chronological age, but would be its metabolomics profile.
4) Of note, the compounds disclosed herein also correlated to spontaneous hemolysis in the units, and thus may also serve as a metric to avoid transfusion of free hemoglobin in patients susceptible to hemoglobin effects.

It is possible that FDA guidelines could be tailored to utilize these specific chemical measurements as release criteria for RBC units. In one embodiment, this application uses a high throughput mass spectrometer. However, alternatively, individual assays could be run on a much smaller platform by traditional assay techniques (i.e. ELISA, enzymatic assay, etc.). Such embodiments would allow a simplified platform with a less elaborate instrumentation. For such purposes, a small number of the above chemical entities that are representative of the whole would be identified and measured. In addition, well described malondialdehyde assays could be used as surrogate for dicarboxylic acids. While malondialdehyde assays are well described, they have not been used for this purpose.

In summary, the present disclosure provides numerous advantages over existing techniques. There are currently no existing techniques to predict post-transfusion survival of RBC units or toxicity of said units

TABLE 1

| Fresh RBCs | p-value | q-value | CORRELATION | Super Pathway | Sub Pathway |
|---|---|---|---|---|---|
| Positive Correlation | | | | | |
| aspartate | 1.11E−06 | 3.00E−04 | 0.71 | Amino Acid | Alanine and Aspartate Metabolism |
| 2'-deoxyuridine | 9.78E−06 | 9.00E−04 | 0.66 | Nucleotide | Pyrimidine Metabolism, Uracil Containing |
| deoxycarnitine | 2.00E−04 | 4.00E−03 | 0.58 | Lipid | Carnitine Metabolism |
| glycylleucine | 3.00E−04 | 4.90E−03 | 0.57 | Peptide | Dipeptide |
| trans-4-hydroxyproline | 4.00E−04 | 5.30E−03 | 0.56 | Amino Acid | Urea cycle; Arginine and Proline Metabolism |
| thymidine | 4.00E−04 | 5.30E−03 | 0.56 | Nucleotide | Pyrimidine Metabolism, Thymine containing |
| isoleucylglycine | 5.00E−04 | 5.80E−03 | 0.55 | Peptide | Dipeptide |
| gamma-glutamyltyrosine | 6.00E−04 | 6.40E−03 | 0.54 | Peptide | Gamma-glutamyl Amino Acid |
| valylglycine | 7.00E−04 | 7.20E−03 | 0.54 | Peptide | Dipeptide |
| N6-acetyllysine | 9.00E−04 | 7.60E−03 | 0.53 | Amino Acid | Lysine Metabolism |
| glutamine | 9.00E−04 | 7.60E−03 | 0.53 | Amino Acid | Glutamate Metabolism |
| N-acetyltaurine | 9.00E−04 | 7.60E−03 | 0.53 | Amino Acid | Methionine, Cysteine, SAM and Taurine Metabolism |
| N-acetylglycine | 1.20E−03 | 9.30E−03 | 0.52 | Amino Acid | Glycine, Serine and Threonine Metabolism |
| 5,6-dihydrothymine | 1.30E−03 | 9.50E−03 | 0.51 | Nucleotide | Pyrimidine Metabolism, Thymine containing |
| Negative Correlation | | | | | |
| palmitate (16:0) | 7.22E−06 | 9.00E−04 | −0.67 | Lipid | Long Chain Fatty Acid |
| glycerol 3-phosphate | 1.40E−05 | 1.00E−03 | −0.66 | Lipid | Glycerolipid Metabolism |
| alpha-ketoglutarate | 2.47E−05 | 1.40E−03 | −0.64 | Energy | TCA Cycle |
| palmitoleate (16:1n7) | 7.92E−05 | 2.80E−03 | −0.61 | Lipid | Long Chain Fatty Acid |
| stearate (18:0) | 9.83E−05 | 2.80E−03 | −0.60 | Lipid | Long Chain Fatty Acid |
| 1-oleoylglycerol (18:1) | 1.00E−04 | 2.80E−03 | −0.60 | Lipid | Monoacylglycerol |
| linoleate (18:2n6) | 1.00E−04 | 2.80E−03 | −0.60 | Lipid | Polyunsaturated Fatty Acid (n3 and n6) |
| eicosenoate (20:1) | 1.00E−04 | 2.80E−03 | −0.59 | Lipid | Long Chain Fatty Acid |
| 10-heptadecenoate (17:1n7) | 2.00E−04 | 4.00E−03 | −0.59 | Lipid | Long Chain Fatty Acid |
| dihomo-linoleate (20:2n6) | 2.00E−04 | 4.00E−03 | −0.58 | Lipid | Polyunsaturated Fatty Acid (n3 and n6) |
| alpha-tocopherol | 2.00E−04 | 4.00E−03 | −0.58 | Vitamin | Tocopherol |
| 4-hydroxy-nonenal-glutathione | 3.00E−04 | 4.90E−03 | −0.57 | Amino Acid | Glutathione Metabolism |
| 20a-dihydroprogesterone | 3.00E−04 | 4.90E−03 | −0.56 | Lipid | Steroid |
| margarate (17:0) | 4.00E−04 | 5.30E−03 | −0.56 | Lipid | Long Chain Fatty Acid |
| 4-methyl-2-oxopentanoate | 4.00E−04 | 5.30E−03 | −0.56 | Amino Acid | Leucine, Isoleucine and Valine Metabolism |
| 2-phosphoglycerate | 5.00E−04 | 5.80E−03 | −0.55 | Carbohydrate | Glycolysis, Gluconeogenesis, and Pyruvate Metabolism |
| oleate (18:1n9) | 5.00E−04 | 5.80E−03 | −0.55 | Lipid | Long Chain Fatty Acid |
| linolenate [alpha or gamma; (18:3n3 or 6)] | 6.00E−04 | 6.40E−03 | −0.55 | Lipid | Polyunsaturated Fatty Acid (n3 and n6) |
| 3-methyl-2-oxobutyrate | 8.00E−04 | 7.60E−03 | −0.53 | Amino Acid | Leucine, Isoleucine and Valine Metabolism |
| cis-vaccenate (18:1n7) | 8.00E−04 | 7.60E−03 | −0.53 | Lipid | Long Chain Fatty Acid |
| 10-nonadecenoate (19:1n9) | 9.00E−04 | 7.60E−03 | −0.53 | Lipid | Long Chain Fatty Acid |
| succinylcarnitine | 1.10E−03 | 8.80E−03 | −0.52 | Energy | TCA Cycle |
| 3-methyl-2-oxovalerate | 1.10E−03 | 8.80E−03 | −0.52 | Amino Acid | Leucine, Isoleucine and Valine Metabolism |
| 2-oleoylglycerol (18:1) | 1.30E−03 | 9.50E−03 | −0.52 | Lipid | Monoacylglycerol |

REFERENCES

1. Dern, R. J., Gwinn, R. P. & Wiorkowski, J. J. Studies on the preservation of human blood. I. Variability in erythrocyte storage characteristics among healthy donors. J Lab Clin Med 67, 955-965 (1966).
2. Dumont, L. J. & AuBuchon, J. P. Evaluation of proposed FDA criteria for the evaluation of radiolabeled red cell recovery trials. Transfusion 48, 1053-1060 (2008).
3. Hess, J. R. Scientific problems in the regulation of red blood cell products. Transfusion 52, 1827-1835 (2012).
4. Reid, T. J., et al. The viability of autologous human red cells stored in additive solution 5 and exposed to 25 degrees C. for 24 hours. Transfusion 39, 991-997 (1999).
5. Dern, R. J. & Wiorkowski, J. J. Studies on the preservation of human blood, IV. The hereditary component of pre- and poststorage erythrocyte adenosine triphosphate levels. J Lab Clin Med 73, 1019-1029 (1969).
6. Silliman, C. C. Lipids: free fatty acids, eicosanoids, and lysophospholipids and the pro-inflammatory effects of transfusion. ASH Meeting 2012 Scientific Program 2012: SCI-48 (2012).

7. Silliman, C. C., et al. Identification of lipids that accumulate during the routine storage of prestorage leukoreduced red blood cells and cause acute lung injury. Transfusion 51, 2549-2554 (2011).
8. Gilson, C. R., et al. A novel mouse model of red blood cell storage and posttransfusion in vivo survival. Transfusion 49, 1546-1553 (2009).
9. Zimring, J. C., et al. Strain-specific red blood cell storage, metabolism, and eicosanoid generation in a mouse model. Transfusion (2013).
10. van de Watering L. Red cell storage and prognosis. Vox Sang 2011; 100: 36-45.
11. van de Watering L. Pitfalls in the current published observational literature on the effects of red blood cell storage. Transfusion 2011; 51: 1847-1854.
12. Fergusson D A, Hebert P, Hogan D L, LeBel L, Rouvinez-Bouali N, Smyth J A, Sankaran K, Tinmouth A, Blajchman M A, Kovacs I L, Lachance C, Lee S, Walker C R, Hutton B, Ducharme R, Balchin K, Ramsay T, Ford J C, Kakadekar A, Ramesh K, Shapiro S. Effect of fresh red blood cell transfusions on clinical outcomes in premature, very low-birth-weight infants: the ARIPI randomized trial. JAMA 2012; 308: 1443-1451.
13. Lacroix J, Hebert P, Fergusson D, Tinmouth A, Blajchman M A, Callum J, Cook D, Marshall J C, McIntyre L, Turgeon A F. The Age of Blood Evaluation (ABLE) randomized controlled trial: study design. Transfus Med Rev 2011; 25: 197-205.
14. Steiner M E, Assmann S F, Levy J H, Marshall J, Pulkrabek S, Sloan S R, Triulzi D, Stowell C P. Addressing the question of the effect of RBC storage on clinical outcomes: the Red Cell Storage Duration Study (RECESS) (Section 7). Transfus Apher Sci 2010; 43: 107-116.
15. Hess J R. Red cell changes during storage. Transfus Apher Sci 2010; 43: 51-59.
16. Hess J R. Red cell storage. J Proteomics 2010; 73: 368-373.
17. Hod E A, Brittenham G M, Billote G B, Francis R O, Ginzburg Y Z, Hendrickson J E. Jhang J, Schwartz J, Sharma S, Sheth S, Sireci A N, Stephens H L, Stotler B A, Wojczyk B S, Zimring J C, Spitalnik S L. Transfusion of human volunteers with older, stored red blood cells produces extravascular hemolysis and circulating non-transferrin-bound iron. Blood 2011; 118: 6675-6682.
18. Hod E A, Spitalnik S L. Harmful effects of transfusion of older stored red blood cells: iron and inflammation. Transfusion 2011; 51: 881-885.
19. Hod E A, Spitalnik S L, Stored red blood cell transfusions: Iron, inflammation, immunity, and infection. Transfus Clin Biol 2012; 19: 84-89.
20. Hod E A, Zhang N, Sokol S A, Wojczyk B S, Francis R O, Ansaldi D, Francis K P, Della-Latta P, Whittier S, Sheth S, Hendrickson J E, Zimring J C, Brittenham G M, Spitalnik S L, Transfusion of red blood cells after prolonged storage produces harmful effects that are mediated by iron and inflammation. Blood 2010; 115: 4284-4292.
21. Kor D J, Van Buskirk C M, Gajic O. Red blood cell storage lesion. Bosn J Basic Med Sci 2009; 9 Suppl 1: 21-27.
22. Silliman C C, Moore E E, Kelher M R, Khan S Y, Gellar L, Elzi D J. Identification of lipids that accumulate during the routine storage of prestorage leukoreduced red blood cells and cause acute lung injury: Transfusion 2011; 51: 2549-2554.
23. Tissot J D, Rubin O, Canellini G. Analysis and clinical relevance of microparticles from red blood cells. Curr Opin Hematol 2010; 17: 571-577.
24. Dumont L J, AuBuchon J P. Evaluation of proposed FDA criteria for the evaluation of radiolabeled red cell recovery trials. Transfusion 2008; 48: 1053-1060.
25. Gilson C R, Kraus T S, Hod E A, Hendrickson J E, Spitalnik S L, Hillyer C D, Shaz B H, Zimring J C. A novel mouse model of red blood cell storage and post-transfusion in vivo survival. Transfusion 2009; 49: 1546-1553.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:
1. A method of testing a red blood cell (RBC) unit for use in a transfusion, the method comprising:
   (a) measuring in a sample from an RBC unit the levels of one or more markers selected from the group consisting of aspartate, 2'-deoxyuridine, deoxycarnitine, glycylleucine, trans-4-hydroxyproline, thymidine, isoleucyl-glycine, gamma-glutamyltyrosine, valylglycine, N6-acetyllysine, glutamine, N-acetyltaurine, N-acetylglycine, 5,6-dihydrothymine, glycerol 3-phosphate, alpha-ketoglutarate, stearate, 1-oleoylglycerol, linoleate, eicosenoate, 10-heptadecenoate, dihomo-linoleate, 4-hydroxy-nonenal-glutathione, 20a-dihydroprogesterone, margarate, 2-phosphoglycerate, oleate, linolenate [alpha or gamma; (18:3n3 or 6)], cis-vaccenate, 10-nonadecenoate, succinylcarnitine, 3-methyl-2-oxovalerate, and 2-oleoylglycerol, and the reticulocyte count of a blood donor at the time of donation,
   (b) comparing the level of the one or more markers in the sample with the level of the one or more markers present in a control sample suitable for transfusion,
   (c) identifying an RBC unit with:
      (i) a lower or the same level of the one or more markers selected from the group consisting of:
      aspartate, 2'-deoxyuridine, deoxycarnitine, glycylleucine, trans-4-hydroxyproline, thymidine, isoleucyl-glycine, gamma-glutamyltyrosine, valylglycine, N6-acetyllysine, glutamine, N-acetyltaurine, N-acetylglycine, and 5,6-dihydrothymine,
      and/or
      (ii) a higher or the same level of the one or more markers selected from the group consisting of:
      glycerol 3-phosphate, alpha-ketoglutarate, stearate, 1-oleoylglycerol, linoleate, eicosenoate, 10-heptadecenoate, dihomo-linoleate, 4-hydroxy-nonenal-glutathione, 20a-dihydroprogesterone, margarate, 2-phosphoglycerate, oleate, linolenate [alpha or gamma;
      (18:3n3 or 6)], cis-vaccenate, 10-nonadecenoate, succinylcarnitine, 3-methyl-2-oxovalerate, and 2-oleoylglycerol, as compared to the corresponding level of the one or more markers present in the control sample suitable for transfusion, and (d) transfusing the RBC unit suitable for transfusion into a subject.

2. The method of claim 1, wherein the measurement is performed at the time of collection of the RBC sample.

3. The method of claim 1, wherein the measurement is performed during the time of storage of the RBC sample.

4. The method of claim 1, wherein the measurement is performed by mass spectrometry.

5. The method of claim 4, wherein the mass spectrometry is gas-chromatography/mass spectrometry (GC/MS) or liquid chromatography-tandem mass spectrometry (LC/MS/MS).

6. The method of claim 1, wherein the measurement is performed by enzymatic assay.

7. The method of claim 1, wherein the measurement is performed by enzyme linked immunosorbent assay (ELISA).

8. The method of claim 1, wherein the level of the one or more marker is 2-200 fold higher than in the control sample.

\* \* \* \* \*